(12) United States Patent
Tucker

(10) Patent No.: US 7,840,250 B2
(45) Date of Patent: Nov. 23, 2010

(54) METHOD FOR NEURAL CURRENT IMAGING

(75) Inventor: Don M. Tucker, Eugene, OR (US)

(73) Assignee: Electrical Geodesics, Inc., Eugene, OR (US)

( * ) Notice: Subject to any disclaimer, the term of this patent is extended or adjusted under 35 U.S.C. 154(b) by 991 days.

(21) Appl. No.: 10/222,536

(22) Filed: Aug. 16, 2002

(65) Prior Publication Data

US 2003/0093005 A1    May 15, 2003

Related U.S. Application Data

(63) Continuation-in-part of application No. 10/001,541, filed on Nov. 13, 2001, now Pat. No. 6,594,521.

(51) Int. Cl.
*A61B 5/00* (2006.01)

(52) U.S. Cl. .................. 600/410; 600/407; 600/411

(58) Field of Classification Search ............... 600/407, 600/410, 411
See application file for complete search history.

(56) References Cited

U.S. PATENT DOCUMENTS

| | | | |
|---|---|---|---|
| 4,123,654 A | 10/1978 | Reiss et al. | |
| 4,202,354 A | 5/1980 | Smith et al. | |
| 4,204,546 A | 5/1980 | Smith et al. | |
| 4,236,511 A | 12/1980 | Loeb | |
| 4,409,987 A | 10/1983 | McIntyre | |
| 4,411,273 A | 10/1983 | John | |
| 4,417,590 A | 11/1983 | Smith et al. | |
| 4,424,816 A | 1/1984 | Callahan et al. | |
| 4,436,684 A | 3/1984 | White | |
| 4,532,591 A | 7/1985 | Osterholm | |
| 4,608,635 A | 8/1986 | Osterholm | |
| 4,690,149 A * | 9/1987 | Ko | 600/409 |
| 4,736,751 A | 4/1988 | Gevins et al. | |
| 4,819,648 A | 4/1989 | Ko | |
| 4,922,915 A | 5/1990 | Arnold et al. | |
| 5,119,816 A * | 6/1992 | Gevins | 600/383 |
| 5,165,410 A | 11/1992 | Warne et al. | |
| 5,291,888 A * | 3/1994 | Tucker | 600/383 |
| 5,303,705 A * | 4/1994 | Nenov | 600/410 |
| 5,307,807 A * | 5/1994 | Sosa et al. | 600/409 |
| 5,390,110 A | 2/1995 | Cheney et al. | |

(Continued)

OTHER PUBLICATIONS

Kiebel et al., Statistical Parametric Mapping for Event-related Potentials, Oct. 16, 2003, NeuroImage 22 (2004) 492-502.*

(Continued)

*Primary Examiner*—Brian Casler
*Assistant Examiner*—James Kish
(74) *Attorney, Agent, or Firm*—Portland Intellectual Property, LLC

(57) ABSTRACT

A method for neural current imaging. Electromagnetic fields produced unknown distribution of unknown sources in the body is sensed at a plurality of remote locations. The inverse problem is solved to produce a first fuzzy "image" of the sources. In addition, a standard imaging method, such as MRI, is used to independently image the body, to obtain a second fuzzy image of the sources. Additional independently obtained fuzzy images may also be provided. All or a selected subset of the images are pooled as components to form an enhanced image with greater resolution or clarity than the component images.

4 Claims, 1 Drawing Sheet

U.S. PATENT DOCUMENTS

| | | | | |
|---|---|---|---|---|
| 5,445,162 | A | * | 8/1995 | Ives .......................... 600/544 |
| 5,458,117 | A | | 10/1995 | Chamoun et al. |
| 5,465,284 | A | | 11/1995 | Karellas |
| 5,482,034 | A | | 1/1996 | Lewis |
| 5,501,230 | A | | 3/1996 | Laribiere |
| 5,630,422 | A | | 5/1997 | Zanakis |
| 5,719,399 | A | | 2/1998 | Alfano et al. |
| 5,807,251 | A | | 9/1998 | Wang et al. |
| 5,807,270 | A | | 9/1998 | Williams |
| 5,810,742 | A | | 9/1998 | Pearlman |
| 5,813,984 | A | | 9/1998 | Haaga et al. |
| 5,816,247 | A | | 10/1998 | Maynard |
| 5,817,029 | A | * | 10/1998 | Gevins et al. ............... 600/544 |
| 5,853,370 | A | | 12/1998 | Chance et al. |
| 5,902,235 | A | | 5/1999 | Lewis et al. |
| 6,009,212 | A | * | 12/1999 | Miller et al. ................ 382/294 |
| 6,041,094 | A | | 3/2000 | Russell |
| 6,330,470 | B1 | | 12/2001 | Tucker et al. |
| 6,529,759 | B1 | * | 3/2003 | Tucker et al. ............... 600/407 |
| 6,606,406 | B1 | * | 8/2003 | Zhang et al. ................ 382/154 |
| 6,609,017 | B1 | * | 8/2003 | Shenoy et al. ............... 600/372 |
| 2003/0081818 | A1 | * | 5/2003 | Fujimaki .................... 382/128 |

OTHER PUBLICATIONS

Dale et al., Dynamic Statistical Parametric Mapping: Combining fMRI and MEG for High-Resolution Imgagin of Cortical Activity, Apr. 2000, Neuron., 26(1), pp. 55-67: (Abstract provided).*

Korvenoja et al., Activation of Multiple Cortical Areas in Response to Somatosensory Stimulation: Combined MEG and fMRI, 1999, Human Brain Mapping, 8(1), pp. 13-27: (Abstract provided).*

Ahlfors et al., "Spatiotemporal Activity of a Cortica Network for Processing Visual Motion Revealed by MEG and fMRI." Nov. 1999.; 82 (5). pp. 2545-2555. (Provided in Full).*

Dale et al., "Improved Localization of Cortical Activity By Combining EEG and MEG with MRI Cortical Surface Reconstruction." 1993. J. Cog. Neuroscsi. 5. pp. 1-20 (Provided in Full).*

Dale et al., Dynamic Statistical Parametric Mapping: Combining fMRI and MEG for High-Resolution Imaging of Cortical Activity, Apr. 2000, Neuron., 26(1), pp. 55-67 (Provided in Full).*

Goldman et al., "Acquiring Simultaneous EEG and Function MRI," 2000, Elsevier, pp. 1974-1980.*

Kamei et al., "Neuronal Current Distribution Imaging Using Magnetic Resonance," Sep. 1999, IEEE Trans On magnetics, vol. 35, No. 5, pp. 4109-4111.*

Thomas R. Gregg, Use of Functional Magnetic Resonance Imaging to Investigate Brain Function, The Graduate School of Biomedical Sciences at The University of Medicine and Dentistry of New Jersey, date unknown.

Allen W. Song, Atsushi M. Takahashi,, Lorentz Effect Imaging, Brain Imaging and Analysis Center and Center for In Vivo Microscopy, Duke University Medical Center, Durham, NC, pp. 763-767, 2001 Elsevier Science Inc.

Shoogo Ueno, Direct Neuronal-Current MRI, University of Tokyo, Japan, IEEE Engineering In Medicine and Biology, May/Jun. 1999, pp. 118.120.

D.M. Schmidt, J.S. George, and C.C. Wood, Bayesian Inference Applied to the Electromagnetic Inverse Problem, Physics Division, Progress Report 1977-1998, pp. 62-29.

Timothy C. Black and William J. Thompson, Bayesian Data Analysis, Computing in Science & Engineering, Jul./Aug. 2001, pp. 86-91.

D.M. Schmidt, J.S. George, D.M. Ranken, and C.C. Wood, Spatial-temporal Bayesian Inference for MEG/EEG, Human Brain Mapping 7, 195 1999.

Kevin H. Knuth, Bayesian Scource Separation and Localization, In: A. Mohammad-Djafari (ed.), SPIE'98 Proceedings: Bayesian Inference for Inverse Problems, SPIE vol. 3459, San Diego, Jul. 1998, pp. 147-158, pp. 10-12.

Sylvain Baillet and Line Garnero, A Bayesian Approach to Introducing Anatomo-Functional Priors in the EEG/MEG Inverse Problem, IEEE Transactions on Biomedical Engineering, vol. 44, No. 5, May 1997.

Kimmo Uutela, Estimating Neural Currents From Neuromagnetic Measurements, Helsinki University of Technology, Systems Analysis Laboratory Research Reports, A83, Dec. 2001, pp. 1-10.

David J. Heeger and David Ress, What Does fMRI Tell Us About Neuronal Activity?, Nature Reviews, Neuroscience, Feb. 2002, vol. 3, pp. 142-151.

* cited by examiner

US 7,840,250 B2

METHOD FOR NEURAL CURRENT IMAGING

RELATED APPLICATIONS

This is a continuation-in-part of U.S. Ser. No. 10/001,541 filed on Nov. 13, 2001, now U.S. Pat No. 6,594,521.

FIELD OF INVENTION

The present invention relates to a method for imaging neural current, for detecting and locating neural activity in the body, and more particularly, in the brain.

BACKGROUND OF INVENTION

It is well known that electrical currents are associated with brain activity. These electrical currents are produced by neurons in the brain and are referred to as "neural currents." Information about neural currents provides a means for understanding brain function. For example, the performance of a specific motor function will involve particular areas of the brain, and the dynamic behavior of the neural currents associated with the motor function provides information about the sequence in which different areas of the brain are involved.

Electroencephalography ("EEG") is a technique that may be used for measuring neural currents. In EEG, electrodes are placed at various locations on the scalp and the difference between the electrical potential at one location and another is measured. If a large number of neurons are concurrently active, it is possible to detect the resulting neural currents. An advantage of EEG is that it has high temporal resolution, i.e., the technique detects the presence of a neural current with only a slight delay from the time when the neurons were active. Because of its high temporal resolution, EEG provides important information about the timing of brain functions. However, a disadvantage of EEG is that it has limited spatial resolution, i.e., it is unable to identify with great accuracy the spatial location of the sources of electrical activity within the brain.

Magnetoencephalography ("MEG") may also be used for detecting neural currents, i.e., by responding to the magnetic fields that are generated thereby. In MEG, the magnetic flux emanating from voltage sources in the brain induces a current in coils that surround the head. The induced current is used to create an image of brain activity. MEG is similar to EEG in that it has the advantage of high temporal resolution and the disadvantage of limited spatial resolution. In addition, the magnetic flux from neural currents is very small relative to background magnetic noise. Therefore, the MEG device must be very sensitive to small magnetic signals, and must be shielded from the background magnetic noise to discern the desired signals. Such shielding is costly to provide, and MEG cannot be used simultaneously with other techniques producing electromagnetic radiations.

Magnetic resonance imaging ("MRI") is most often used for measuring blood flow or blood oxygenation levels within the brain. The technique is based on the principles of nuclear magnetic resonance ("NMR") and a brief explanation is necessary to understanding.

Most atomic nuclei possess a nonzero nuclear spin quantum number and a coaxial magnetic moment about a corresponding spin axis. The nuclei may be characterized as magnetized gyroscopes. Just as for the angular momentum vector of a gyroscope in a gravitational field, the vector moments of the nuclei precess about their spin axes in the presence of a magnetic field at a frequency ("Larmor frequency") that is proportional to the magnetic moment of the nuclei multiplied by the magnitude of the magnetic field.

The vector moments of the precessing nuclei trace a cone in space describing an angle with respect to the direction of the magnetic field. Where there are many nuclei, such as in the body, the vectors sum to a single, ensemble moment aligned with the magnetic field, the lateral vector components averaging out.

In MRI, a large, static first magnetic field is applied to a body. This causes the ensemble moment of the nuclei in the body to align with the direction of the first magnetic field, as the nuclei precess at the Larmor frequency. In addition, a second, alternating magnetic field is applied to the body in a direction perpendicular to the direction of the first magnetic field. The frequency of the second magnetic field is adjusted to match the Larmor frequency. In that special circumstance, the nuclei precess about the direction of the second magnetic field as though the static field were absent. Thence, as a result of the application of the second magnetic field at the Larmor frequency, the ensemble moment tips away from being aligned with the first magnetic field.

The second magnetic field is produced as transmitted electromagnetic radiation at radio frequency (RF). It is typically provided as a pulse. The amount of tipping can be controlled by the duration of the pulse, it being desirable to rotate the ensemble moment from alignment with the static field $\pi$2 radians. When the pulse is turned off, the ensemble moment relaxes ("spin relaxation"), or loses energy, so that it re-aligns with the static field.

This relaxation occurs through two kinds of energy loss mechanisms: spin-spin interactions and spin-lattice interactions (where the term "lattice" is used loosely in the context of liquids or other noncrystalline environments). Because the energy states for the spin angular momenta are quantized, these interactions must permit precise amounts of energy loss or relaxation cannot occur, and due to the randomness of the interactions, it results that a substantial time is required for relaxation.

The rate of relaxation for a given atomic nucleus depends on magnetic field fluctuations caused by its neighbors as a result of thermal agitation. Particularly, spin-lattice interactions cause the energy provided by the RF pulse to decay exponentially with a time constant $T_1$, and decay due to spin-spin interactions is described by an associated time constant $T_2$. Where the fluctuations occur at rates that are either to large or too small compared to the Larmor frequency, energy dissipation is inefficient and therefore slow, resulting in long decay times $T_1$ and $T_2$.

In order to measure the times T, it is noted that energy lost in the transition of an atomic nucleus from a higher energy state (corresponding to precession due to the second, alternating magnetic field) to a lower energy state (corresponding to spin relaxation) produces radiation at the frequency defined by the energy difference between the energy states. For protons in body tissue, this radiation (termed "free induction signal") is in the radio frequency range and is detected with a coil as an electrical signal indicative of the decay times T.

The RF pulse excite all the atomic nuclei at once. The free induction signal that follows has a highly complex time dependence. However, this complex decay waveform can be Fourier transformed to provide discernible NMR spectra indicative of the type and amount of atomic nuclei, as well as their atomic environment. From this spectroscopic information, tissue type can be determined.

Even so, the spectra do not contain any spatial information so that an image cannot yet be formed. To solve this problem, magnetic field gradient ("MFG") pulses are used to spatially encode the free induction signals, to provide for locating the atomic nuclei responsible for the measured spectra in space. The MFG pulses are spatially varying magnetic fields generated by coils. The pulses are aligned with the first, static magnetic field and provide a linear gradient to the field along the x, y, or z axis. For a linear gradient in the z direction, for example, all points on the x and y axes will see the same magnetic field, providing a planar "slice" of data corresponding to that value of the first magnetic field. Where the first magnetic field is altered due to the gradient, the Larmor frequency is altered, and there will not be resonance with the second, alternating magnetic field. To image another slice, the second, alternating magnetic field can be adjusted.

An advantage of MRI is that it provides images with good spatial resolution. A disadvantage of MRI is that the time required for spin relaxation, even the relatively short time required for relaxation of protons in lipids, limits the temporal resolution of MRI.

It has been proposed to directly measure neural currents using MRI. The proposed technique is referred to herein as Magnetic Resonance Neural Current Imaging ("MRNCI"). One method is based on the principle that a current-carrying conductor experiences a force (a Lorentz force) when it is placed in a magnetic field. The magnitude of the force is proportional to the amount of current and the strength of the magnetic field. The direction of the force is perpendicular to the direction of current flow. A conductor that is not rigidly confined will be displaced in the response to the Lorentz force.

Neural currents flow through nerve cells which are therefore current-carrying conductors. Accordingly, nerve cells may be displaced by applying a magnetic field in proportion to the amount of neural activity carried thereby. If this displacement is large enough, it may be seen using imaging techniques such as MRI. However, the amount of neural current is very small, so to obtain a detectable displacement requires a very large magnetic field MRI devices are capable of producing very large magnetic fields, and could also be used according to MRNCI to produce images before and during a period of neural activity. The images would be compared by subtraction to produce a new image showing tissue displacement. However, MRNCI has not yet been shown to be able to detect currents as small as neural currents. The magnitude of such currents is of the same order of magnitude as the noise limits of modern MRI systems. Thus, successful implementation of MRNCI as proposed will require increasing the sensitivity of MRI measurements.

Moreover, the time required for obtaining an MRI image is substantially greater than the time required for accurate characterization of neural activity. The spin relaxations occur over a period of time on the order of 50 ms, the entirety of which must be taken to obtain all the data corresponding to a single "snapshot" or image slice. On the other hand, neural currents may only exist for time periods on the order of 1 ms, so that the physical displacement of the current-carrying conductor ceases before the MRI has had sufficient opportunity to "see" it.

The problem of detecting and therefore locating sources of neural activity is a subset of the problem of locating remote sources of electrical activity generally. The sources responsible for producing, for example, EEG data, are generally inaccessible to being probed directly. Therefore, the location and characteristics of these sources must be inferred from the fields they produce outside the body. Deducing the source magnitudes and spatial coordinates from measurements on such fields is known as "solving the inverse problem," i.e., reconstructing the sources and their distribution from the results that they are known to have produced.

For a limited number of sensors, the data produced thereby are inherently ambiguous, in that a number of different solutions to the inverse problem can fit the data. The number of possible solutions is reduced by using more sensors and by sensing with greater precision; however, there is a practical limit to improving resolution, and therefore limiting the number of potential solutions to the inverse problem by improved means for sensing alone.

Methods facilitating solving the inverse problem have been developed by the present inventor, along with others, which are described in U.S. Pat. No. 6,330,470. These methods not only sense the electromagnetic fields generated by sources within the body, but reciprocally stimulate them as well to produce additional information about their location. These methods may be anticipated to be useful for neural current analysis by providing an improved tool for solving the inverse problem, but solving this problem to a high degree of resolution for extremely weak sources is inherently difficult.

In a paper entitled "Bayesian Inference Applied to the Electromagnetic Inverse Problem," D. M. Schmidt et al. have proposed a method for solving the inverse problem for sources of neural current. Basically, the proposed method begins by assigning probabilities to possible locations of neural current activity by using anatomical data, physiological data, or results from measurements such as MRI or PET (positron emission tomography). Rather than solving the inverse problem, therefore, the method provides an educated guess. For example, it may be surmised that particular neural activity would occur in the cortex, and the location of the cortex is known from anatomical data. Next, EEG (electroencephalograph) or MEG (magnetoencephalograph) data are acquired such as mentioned above. Finally, Bayesian statistics are used to estimate the post-acquisition probabilities for the possible locations of neural activity given their pre-acquisition probabilities as determined above. While some success for the method has been reported, neural current imaging remains inherently difficult due to the weakness of the sources and improved methods are being sought.

Accordingly, there is a need for a method for imaging neural currents that offers improved spatial and temporal resolution.

BRIEF SUMMARY OF THE INVENTION

Disclosed herein is a method for neural current imaging. Within the scope of the invention, electromagnetic fields produced unknown distribution of unknown sources in the body is sensed at a plurality of remote locations. The inverse problem is solved to produce a first fuzzy "image" of the sources. In addition, a standard imaging method, such as MRI, is used to independently image the body, to obtain a second fuzzy image of the sources. Additional independently obtained fuzzy images may also be provided. All or a selected subset of the images are pooled as components to form an enhanced image with greater resolution or clarity than the component images.

Preferably, the data corresponding to the first and second images are acquired substantially simultaneously.

Preferably, the data corresponding to the first image is obtained by sensing, exterior to the body, the electromagnetic fields produced by the neural current sources.

Preferably, sensors used to obtain the data corresponding to the first image are arranged substantially as the vertices of a geodesic sphere.

Preferably, the data corresponding to the first image is obtained by a combination of sensing voltage and injecting current, or the converse.

Preferably, the data corresponding to the second image is obtained by MRI.

Accordingly, it is an object of the present invention to provide a novel and improved method for neural current imaging.

It is another object of the present invention to provide such a method providing improved spatial and temporal resolution.

The foregoing and other objectives, features, and advantages of the invention will be more readily understood upon consideration of the following detailed description of the invention, taken in conjunction with the accompanying drawings.

DETAILED DESCRIPTION OF A PREFERRED EMBODIMENT

A preferred method for imaging neural currents according to the present invention is described below, along with the preferred application of determining the spatial and temporal parameters or coordinates of neural currents in the brain. However, it should be understood that methods according to the invention may be used generally to improve the clarity or precision of any data and are therefore not limited to neural current imaging. Moreover, methods according to the present invention may be used for imaging any electrophysiological activity in which current flows, such as heart electrical activity.

Figure 1:
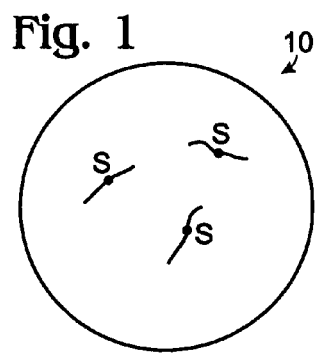
FIG. 1 is a schematic view of a head, showing sources of neural current activity therein.

Referring to FIG. 1, a portion 10 of a body, such as a human head, is shown with sources "S" inside that are representative of neural activity. Particularly, the sources "S" represent nerve cells that carry neural currents from one interior location in the head to another. The neural activity can result from a voluntary or involuntary motor function, or be a result of thought.

The moving charges that define the currents produce a time varying electromagnetic field that in theory could be measured at the scalp 11, such as with EEG apparatus. However, the currents are so small, in relation to ambient electromagnetic noise, that it is very difficult to discern this field in this manner. Accordingly, it is generally not practical to obtain sufficient resolution by solving the inverse problem for locating these sources in the standard manner.

Tucker, in U.S. Ser. No. 10001,541, incorporated by reference herein in its entirety, discloses an improved method for solving the inverse problem that not only senses the electromagnetic fields produced by sources within the body, but reciprocally stimulates them as well to produce additional information ("data") useful to determining their location. The method of the present invention preferably makes use of data obtained according to this methodology; however, any prior art methodology for sensing electromagnetic fields produced by the sources "S" may be employed without departing from the principles of the invention. While described below in terms of EEG methodologies, MEG methodologies may also be used, since the sources produce both electric and magnetic field distributions.

Figure 2:
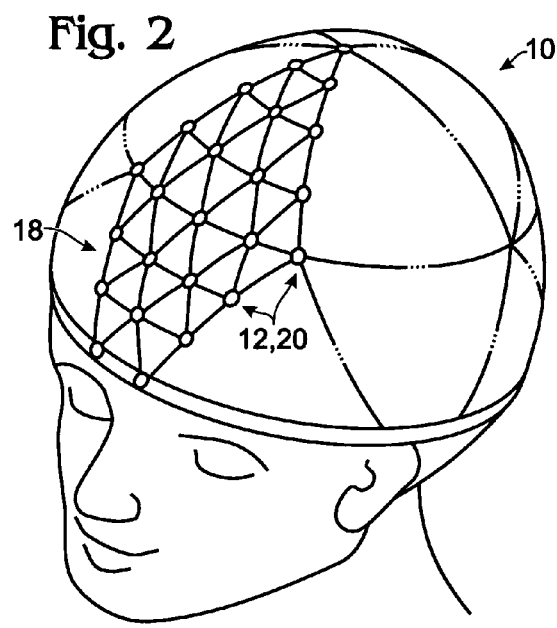
FIG. 2 is a pictorial view of the head of FIG. 1 provided with sensors according to the present invention for producing data responsive to the neural current activity.

Referring to FIG. 2, according to the preferred methodology, sensors 12 are distributed over a selected portion of the surface of the body 10. The sensors 12 are assembled in a carrier 18 which spaces the sensors apart from one another in a predetermined manner. A preferred carrier is that described in Tucker, U.S. Pat. No. 5,291,888 (hereinafter the "geodesic sensor net"), the entirety of which is incorporated herein by reference. The geodesic sensor net places a sensor at the vertices of geodesic triangles by elastic lines connecting the sensors in a mutually-balanced tension network. While the geodesic sensor net is preferred, any apparatus suitable for acquiring electromagnetic field data at the scalp 11 or elsewhere remote from the sources "S" may be employed.

Preferably, the array includes 128 or 256 sensors with approximately equal spacing between adjacent pairs. A greater number of sensors provides for a greater spatial resolution.

The sensors are typically adapted to sense voltage, but can be adapted to sense current as well. To simplify discussion, the sensors will be described herein as being adapted to sense voltage, the complementarity of voltage and current being understood.

The sensors functioning together to sense their respective voltages provide a map of potential as a function of location on the body surface. To localize the sources inside the body that are responsible for the measured potential function, a computer "body model" is made of the interior of the body. In the body model, the body is partitioned into a number of homogeneous tissue volumes of differing tissue types. The body model may be relatively simple, assuming for example a small number of concentric spherical shells of the differing tissue types, or the body model may be more complex, such as a finite-element model. Voltage sources, the number and strengths of which must be selected by trial and error, are also modeled, typically as single or multiple dipoles, or extended dipolar sheets, and mathematically placed within the body model.

The computer then calculates the potential that would result at the surface of the body model with the given sources and this result is compared to the actual, measured potential function on the body 10. Where there is disagreement, the sources are iteratively moved andor their characteristics are adjusted to reduce the error to an acceptable level. This modeling process is well known in the art and further details are omitted as not being necessary for understanding.

To calculate the potential that would result at the surface of the body model from the modeled sources requires specification of the conductivity or, more generally, the impedance, of the modeled tissue. Where the model is a simple model, a small number of different impedance values is required. Where the model attempts greater resolution, a larger number of impedance values is required, each being characteristic of a particular volume of the body model.

The impedance values may be measured by researchers and published as data for inclusion in the computer body model. However, as published values obtained from measurements on a small number of individuals, the impedance values are not generally correct for the particular body 10.

Preferably, the sensors 12 are replaced with electrical devices 20 adapted both for measuring voltage (or current) and applying current (or voltage). The devices 20 are typically adapted to sense voltage, typically in the microvolt range, and apply current, typically in the microamp range, but may be adapted to sense current and apply voltage as well. To simplify discussion, the devices will be described as sensing voltage and applying current, the complementarity of voltage and current being understood.

The electrical devices 20 may be simple metal electrodes suitably coupled to a suitable volt-meter and current source. The electrical devices 20 are employed in a measurement mode just as the prior art sensors 12. However, in an injection mode, the electrical devices apply a current to the surface of the body.

More particularly, each electrical device forms a port with a selected reference device. According to the invention, some of the ports are employed for sensing the potential on the surface of the body resulting from electrical activity within the body, as in the prior art. These same ports are also employed for sensing the potential on the surface of the body resulting from injecting current into the remaining ports. This latter step provides data for characterizing the impedance of the body volume in an analogous manner to that aforedescribed for characterizing the locality of sources.

The aforementioned current injection is preferably performed at a frequency or frequencies selected to be distinct from the frequency or frequencies of known body sources, so that the corresponding voltages sensed can be identified as resulting from the injected current. Once impedance values for the body 10 are obtained for use in the body model, the aforementioned prior art localization method may be employed.

If both the impedance characterization method and the localization method described above are carried out with the same apparatus, i.e., the same carrier 18 and electrical devices 20, significant improvements in localization accuracy are obtained. Particularly, the reciprocity theorem, i.e., that for a passive network, that if injecting a current into (or applying a voltage across) a first port produces a voltage (or current) at a second port in response, the same voltage (or current) would be produced at the first port if the same current was injected into (or the same voltage was applied across) the second port, suggests that the same conductive paths inside the mass of body tissue are used for conducting current from a source of electrical activity thereinside to the surface, as are used in conducting current injected at the surface to the electrical source, where injecting current at the body surface is just the aforedescribed method of impedance characterization. Accordingly, so long as the same electrical devices are used in potential measurement for impedance characterization as in potential measurement for source localization, the impedance characterization is automatically tailored to account for the precise electrical pathways inside the body mass, from the electrical sources there, to the surface of the body mass where a potential measurement is made for purposes of source localization. Where the method is carried out in this way, one does not need to know about the details of the body mass to localize sources therein to an accuracy which is limited only by the resolution provided by the number of electrical devices employed.

Alignment of the sensors is provided automatically by electrical devices 20 that are adapted for both measurement and application in conjunction with a carrier 18 that substantially fixes the locations of the electrical devices on the body for at least the period of time during which both sets of measurements are being made.

Regardless of the method used to acquire data determining the electromagnetic fields produced by the sources "S" ("source field data"), the data is used to localize the sources, i.e., to solve the inverse problem, to a degree of uncertainty, to produce a first fuzzy "image" of the sources S. Where the aforedescribed improvement in source localization methodology is employed, the uncertainty may be greatly reduced, but some uncertainty is assumed to nevertheless remain.

Figure 3:
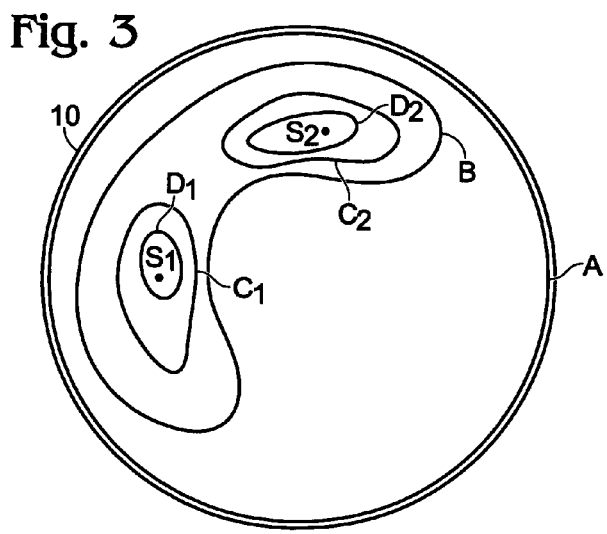
FIG. 3 is a schematic view of a head, showing probability contours for the location of sources of neural current activity therein.

The fuzziness of or uncertainty in the images may be conceptualized as contour lines of probability. For example, referring to FIG. 3, there is a 100% probability that the sources $S_1$ and $S_2$ are somewhere inside the head 10, and therefore within the contour A. There may be a 90% probability that the sources are within the cortex defined by contour B, an 80% probability that the source $S_1$ is in within the contour $C_1$ and the source $S_2$ is within the contour $C_2$, a 60% probability that the source $S_1$ is in within the contour $D_1$ and the source $S_2$ is within the contour $D_2$, and so on. As the contour lines become closer together and converge on the sources S, the resolution or clarity of the image of the sources is increased.

Because the first image is assumed to lack the desired resolution or clarity, according to the invention an imaging method is used to obtain a second image of the sources.

There are many known imaging methods, and new imaging methods are being developed all the time. As has been pointed out above, MRI is a standard imaging method that senses RF pulses indicative of spin relaxation following induced spin energy absorption and is a preferred method due to its availability. For any method that creates images of local neuronal activity based on magnetic resonance techniques, the present invention offers improvement of the imaging through the integration of remote electrical measures from the head or body surface.

Where the sources or their electrical activities are evanescent or fleeting, such as is the case for neural currents, the imaging method is preferably carried on substantially simultaneously with remotely sensing the electromagnetic fields such as described above, so that the second image provides an independent view of the same sources and the same electrical activity seen in the first image. As one of the methods is typically faster than the other, substantial simultaneity therefore means that at least some sense measurements for each method are being made at the same time. Where MRI is used as the imaging method, the apparatus used "in the magnet" to collect the source field data should be formed of nonmagnetic materials. For example, EEG data may be collected with nonmagnetic electrodes during MRI. Where MEG methodologies are employed in conjunction with MRI, the MEG data cannot be obtained during MRI because of the magnetic fields produced by the magnet.

Like the "image" obtained from the source field data, the image obtained by the imaging method is also assumed to be uncertain or "fuzzy," due to the weakness of the sources being imaged. Additional independently obtained fuzzy images may also be used to provide additional information about the sources and their location.

According to the invention, all or a selected subset of the independent images are pooled as components to form an enhanced image with greater resolution than the component images. This may be done by using a number of different techniques; for example, the image data may be made available in digital form so that it can be operated on mathematically or statistically with a computer. The enhanced image may be formed simply by averaging the data for two or more fuzzy images, pixel-by-pixel. The average may be a weighted average taking into account the expected or known resolution of the respective images. Bayesian inferential methods may be employed as well. Bayes' rule results from the product rule of probability for the probability of A and B given background information I:

$$P(A,B|I) = P(A|B,I) \cdot P(B|I) = P(B|A,I) \cdot P(A|I). \tag{1}$$

Therefore, $$P(A|B,I) = P(A|I) \cdot P(B|A,I)/P(B|I), \tag{2}$$

where P(A|B,I), termed the posterior probability, is the probability of the hypothesis A after considering the effect of evidence B and background information I. P(A|I) is the prior probability of A assuming the background information I is true but before knowledge of the evidence B; P(B|A,I) is the probability of the evidence B assuming that the hypothesis A and the background information I are true; and P(B|I), is the prior probability of the evidence B assuming the background information I is true independent of the hypothesis A.

To apply Bayes' rule to enhance image B using image A, identify the data corresponding to the image A as the prior probability of the image A given the neural current activity I, identify the data corresponding to the image B as the prior probability of the image B given the same neural current activity I, and solve for the posterior probability of the image B in light of image A and neural current activity I. It is reasonable to assume that the data corresponding to image A is "true" even though its resolution is not necessarily high.

While particularly useful for neural current imaging, the resolution of other images or data sets may be enhanced according to the principles of the invention.

The terms and expressions that have been employed in the foregoing specification are used as terms of description and not of limitation, and are not intended to exclude equivalents of the features shown and described or portions of them. The scope of the invention is defined and limited only by the claims that follow.

The invention claimed is:

1. A method for imaging electrical current flowing in a body, the current defining a field outside the body, the method comprising:
    obtaining field data, by use of at least one of (a) EEG and (b) MEG, representative of the field at a selected time;
    obtaining a solution to the inverse problem posed by said field data;
    producing, based on said solution, a first image showing the current at a first resolution;
    scanning the body at the same said time as part of an MRI procedure;
    producing by said MRI procedure a second image showing the current at a second resolution; and
    combining said first and second images so as to produce an enhanced image of the current at a third resolution that is greater than the first and second resolution.

2. The method of claim 1, wherein said step of combining comprises employing Bayesian inference.

3. The method of claim 2, wherein the current is neural current.

4. The method of claim 1, wherein the current is neural current.

* * * * *